United States Patent

Bach

[11] Patent Number: 6,113,924
[45] Date of Patent: Sep. 5, 2000

[54] MOISTURE-BINDING SKIN CARE PRODUCT AND METHOD OF MAKING THE SAME

[75] Inventor: Marlene Bach, Buehl, Germany

[73] Assignee: Fribad Cosmetics GmbH, Baden-Baden, Germany

[21] Appl. No.: 08/597,516

[22] Filed: Mar. 19, 1996

Related U.S. Application Data

[63] Continuation of application No. 08/277,695, Jul. 1, 1994, abandoned.

[51] Int. Cl.[7] .......................... A61K 7/00; A61K 9/107; A61K 9/113
[52] U.S. Cl. .......................... 424/401; 514/937; 514/938
[58] Field of Search .......................... 424/401; 514/937, 514/938

[56] References Cited

U.S. PATENT DOCUMENTS

| 4,254,104 | 3/1981 | Suzuki | 514/938 |
|---|---|---|---|
| 4,331,167 | 5/1982 | Wajaroff | 132/7 |
| 4,438,095 | 3/1984 | Grollier et al. | 424/70 |
| 4,776,976 | 10/1988 | Nakamura | 252/312 |
| 4,782,095 | 11/1988 | Gum | 514/937 |
| 5,036,108 | 7/1991 | Asahi | 514/938 |

FOREIGN PATENT DOCUMENTS

| 0 014 479 | 8/1980 | European Pat. Off. . |
| 2163541 | 7/1972 | Germany . |
| 2905257 | 8/1980 | Germany . |
| 3110258 | 2/1982 | Germany . |

OTHER PUBLICATIONS

Janistyn, H. ,"Handbuch Der Kosmetika Und Riechstoffe III Band: Die Körperpflegemittel", Dr. Alfred Hüthig Verlag Heidelberg, pp. 605–611. (Translation–partial.).

*Primary Examiner*—Thurman K. Page
*Assistant Examiner*—Lakshmi Channavajjala
*Attorney, Agent, or Firm*—Venable; George H. Spencer; Ashley J. Wells

[57] ABSTRACT

A skin care product which is moisture-binding, which has a pH ranging between 7.2 and 7.6, and which is a three-phase product consisting of a water phase and an oil/water emulsion creamed up and floating on top of the water phase, and which maintains this three-phase state for at least one year, and a method of making same which includes providing a water phase comprised of at least one cosmetically active ingredient which is water-soluble, and solvents including water, at least one glycol and at least one alcohol which is not a glycol; providing an oil phase comprised of at least one cosmetically active ingredient which is oil-soluble, and at least one emulsifying agent; heating separately the water phase and the oil phase; mixing the water phase and the oil phase which have been heated to provide a mixture having a temperature ranging between 37° and 44° C.; cooling the mixture to a temperature ranging between 26° and 30° C. while stirring the mixture under a vacuum; homogenizing the mixture after cooling for a time period ranging from one half minute to 3 minutes; and allowing the mixture to settle and to separate after homogenization within a period which does not exceed 8 hours to provide the three-phase product.

12 Claims, No Drawings

MOISTURE-BINDING SKIN CARE PRODUCT AND METHOD OF MAKING THE SAME

This application is a Continuation of application Ser. No. 08/277,695, filed Jul. 1,1994 (now abandoned).

BACKGROUND OF THE INVENTION

Field of the Invention;

The invention relates to a method of making a moisture-binding skin care product on the basis of an oil-in-water emulsion, wherein the water phase and the oil phase are mixed at an elevated temperature and then cooled while stirring and to the products made with this method.

Such a skin care product is known from European Patent 0 258 558 B2. This skin care product consists, in the resting state, of a separate oil-in-water emulsion (o/w emulsion) which is on top of an aqueous phase. This skin care product is especially characterized by the fact that it is free of emulsion stabilizers and that the emulsifying agent is added at a proportion of $\leq 1\%$. A general formulation of this product consists of approx. 10 to 90% lipophilic constituents, approx. 90 to 10% hydrophile constituents and preferably approx. 0.01 to 0.5% emulsifying agent.

Just prior to applying this product to the skin, it is shaken. This results in an unstable oil-in-water emulsion. It was observed at this point that this product corresponds to an o/w emulsion with regard to its spreadability and the individual sensation of the user, while, at the same time, accomplishing the moisture-binding and protective effect of a w/o emulsion. Thus, this skin care product features both the positive characteristics of an o/w emulsion and the favorable characteristics of a w/o emulsion.

As mentioned above, an unstable oil-in-water emulsion is formed after shaking the product. Regarding this point, European Patent 0 258 558 explains further that, after a relatively short period, a phase separation occurs in the forming unstable emulsion in a manner which results in an o/w emulsion with an aqueous phase.

It became evident, however, that the separation into the oil-in-water emulsion and the aqueous phase does not always occur. It became evident, in particular, that, in many cases, a separation into the afore-described phases either did not take place at all or took place only after a very long time (several weeks). A further disadvantage is the fact that the afore-described phases were not stable, i. e., that a further separation of the oil-in-water emulsion took place. A separation into three phases was also observed, i. e., a water phase, the o/w emulsion and an oil layer. For the consumer, however, it is important, also for visual reasons, that the shaking take place starting from an o/w emulsion which is on top of an aqueous phase.

Departing from this basis, it is the object of the present invention to propose a method of making a skin care product according to European Patent 0 258 558, which makes it possible for the resulting skin care product to have a stable o/w emulsion in its resting state on top of an aqueous phase over an extended period of time (at least one year), wherein the formation of the o/w emulsion and the water phase is to take place within a few hours after shaking.

SUMMARY OF THE INVENTION

This problem is solved with regard to the method by providing a method of making a moisture-binding skin care product by mixing a water phase containing, apart from water, water-soluble active ingredients, glycols, alcohols, preservatives and, as the case may be, dyes, with an oil phase containing oil-soluble active ingredients, preservatives, emulsifying agent and, as the case may be, perfume, characterized by the combination of the following process steps: a) in that the water phase and the oil phase are heated separately, are mixed at an elevated temperature and set to a temperature of 37° to 44° C., b) in that the mixture is cooled down to 26° to 30° C. while stirring and under vacuum, and c) in that homogenization takes place at 26° to 30° for a duration of one half minute to 3 minutes. With regard to the skin care product itself, this problem is solved by providing a moisture-binding skin care product made according to the above method characterized in that the pH is between 7.2 and 7.6. Advantageous modifications appear in the dependent claims.

Surprisingly, Applicant could show that by complying with certain precisely selected process parameters a skin care product of the generic type can be made consisting of an emulsion phase (approx. ⅓) and an aqueous phase (approx. ⅔). It is particularly surprising and unexpected that this state already comes about after a few hours (4 to 8 hours) and that this state is maintained over an extended period of time (at least one year). Since, based on the laws of thermodynamics, the oil and water phase must demulsify again, it could not be expected that this intermediate state in the form of an o/w emulsion on top of a water phase could be stably maintained for such a long time, obviously, there is a "creaming up" of the unstable emulsion.

This is achieved according to the invention by combining various process steps. First, the separate water phase and the oil phase are heated and brought together at an elevated temperature and the mixture is then set to 37° to 44° C. Here, the preferred temperature of the mixture, i. e., the water and oil phase, is at 38°–42° C., particularly preferable at 41° C. It is decisive for the method according to the invention that, in a second process step, this mixture is cooled while it is simultaneously stirred under vacuum conditions. Preferably, the mixture is cooled down to a temperature of 27° to 29° C. The vacuum is in the range of 0.3 to 0.5 atm. The mixture is stirred with a stirrer at a speed of 30 r.p.m. All stirrers known from prior art may be used, such as, for example, anchor screws. In a last process step (characteristic c), homogenization takes place for a duration of 0.5 to 3 minutes at the temperature to which the mixture is cooled during the cooling phase. Homogenization preferably takes place for a duration of 1 to 1.5 minutes. The rotational speed of the homogenizer may be in the range of 1,500 to 2,500, preferably at 1,500.

In practical experiments it could be shown that the desired phase separation described above and the stability of these phases can only be accomplished if the above-described procedural sequence, particularly with regard to the specified temperature ranges, is adhered to precisely.

From a material point of view, the method according to the invention comprises all of the compounds already mentioned in European Patent 0 258 558. Reference is therefore made expressis verbis to the disclosure content of this document. In particular, the aqueous phase may contain, in addition to water, especially water-soluble active ingredients, glycols, alcohols, preservatives and, as the case may be, dyes. The oily phase may contain, in particular, oil-soluble active ingredients, preservatives, the emulsifying agent and, as the case may be, perfume.

The specific amount of emulsifying agent is determined by its HLB value (hydrophile lipophile balance) and the mixing ratio of aqueous and oily phase. But, at most, a portion of up to 1% of emulsifying agent is added. All emulsifying agents known so far from prior art may be used. In this context, the use of trilaneth-4-phosphate is particularly preferable.

Furthermore, the invention relates to the skin care products made with the above-described method. The skin care products made by means of this method are characterized in that their pH is between 7.2 and 7.6. The viscosity levels are preferably between 170 and 190 mPA, and the density between 0.9850 and 0.9890.

DESCRIPTION OF THE PREFERRED EMBODIMENTS

In the following, the method is described in greater detail with reference to an embodiment.

Embodiment:

| First, the water phase is made, consisting of: | |
|---|---|
| aqua demin. | 39.25% |
| hyaluronic acid | 0.10% |
| mannuronic acid silanol | 20.00% |
| plant extract | 13.00% |
| D-panthenol | 2.00% |

The oil phase is prepared separately from the water phase and contains the following ingredients:

| avocado oil | 20.00% |
|---|---|
| vitamin E acetate | 5.00% |
| perfume | 0.25% |
| preservative | 0.30% |
| trilaneth-4-phosphate | 0.10% |

The water and the oil phase are heated separately; the water phase to 52° C. and the oil phase to 40° C.

The two above-described phases are brought together at 41° C. in a vessel that can be cooled and evacuated. A vessel of the type MMK 150 of the Krieger company was used as a vessel that was capable of being cooled and evacuated. Immediately after bringing together the water and the oil phase, the mixture is cooled down to 28° C. in a vacuum while stirring. The mixture was stirred with a stirrer made by Krieger at a speed of 35 revolutions per minute. The cooling phase is stopped when exactly 28° C. are reached. After the cooling phase, homogenization takes place for a duration of 1.5 minutes. Homogenization takes place with a homogenizer of the Krieger type. The speed of the homogenizer is 1,500 r.p.m.

After the homogenization is completed, the product is filled into the corresponding containers. In a product made in this manner, a separation into an oil-in-water phase (approx. ⅓) and an aqueous phase (approx. ⅔) takes place within eight hours. Tests in practice have shown that this phase remained stable over a long period of time (longer than one year). After shaking, a return to the above-described state occurred within a period of 6 to 7 hours.

The product according to this embodiment has a viscosity of 180 mPA/sec, a density of 0.9860 and a pH of 7.4.

What is claimed is:

1. A method of making a skin care product which is moisture-binding, which is a three-phase product consisting of a water phase and an oil/water emulsion creamed up and floating on top of the water phase, and which maintains said three-phase state for at least one year, comprising:

a. providing a water phase comprised of at least one cosmetically active ingredient which is water-soluble and solvents comprising water, at least one glycol and at least one alcohol which is not a glycol;

b. providing an oil phase comprised of at least one cosmetically active ingredient which is oil-soluble, and at least one emulsifying agent in an amount ranging up to 1% by weight based on total weight of the skin care product;

c. heating separately the water phase and the oil phase;

d. mixing the water phase and the oil phase which have been heated to provide a mixture having a temperature ranging between 37° and 44° C.;

e. cooling the mixture to a temperature ranging between 26° and 30° C. while stirring the mixture under a vacuum;

f. homogenizing the mixture after cooling for a time period ranging from one half minute to 3 minutes; and g. allowing the mixture to settle and to separate after homogenization within a period which does not exceed 8 hours to provide the three-phase product consisting of a post homogenization water phase and an oil/water emulsion creamed up and floating on top of the water phase.

2. The method according to claim 1, wherein heating separately the water phase and the oil phase in step (c) continues until temperatures ranging from 38° to 42° C. are achieved.

3. The method according to claim 1, wherein the mixture is cooled in step (e) to a temperature ranging from 27° to 29° C.

4. The method according to claim 1, wherein the mixture is stirred in step (e) at a stirrer speed ranging from 15 to 50 rpm.

5. The method according to claim 4, wherein the mixture is stirred in step (e) at a stirrer speed ranging from 20 to 40 rpm.

6. The method according to claim 1, wherein the mixture is homogenized in step (f) at a homogenizer speed ranging from 1,500 to 2,500 rpm.

7. The method according to claim 1, wherein the mixture is homogenized in step (f) for a time period ranging from 0.5 to 3 minutes.

8. A skin care product which is moisture-binding, which has a pH ranging between 7.2 and 7.6, which is a three-phase product consisting of a water phase and an oil/water emulsion creamed up and floating on top of the water phase, and which is made by the method according to claim 1.

9. The skin care product according to claim 8, wherein the skin care product has a density ranging between 0.9850 and 0.9890.

10. The skin care product according to claim 8, wherein the skin care product has a viscosity ranging between 170 and 190 mPa.

11. The method according to claim 1, wherein the water phase further comprises at least one material selected from the group consisting of (A) at least one preservative and (B) at least one dye.

12. The method according to claim 11, wherein the oil phase further comprises at least one material selected from the group consisting of (A) at least one preservative and (B) at least one perfume.

* * * * *